(12) United States Patent
Fein et al.

(10) Patent No.: US 6,749,834 B2
(45) Date of Patent: Jun. 15, 2004

(54) METHODS AND APPARATUS FOR THERAPEUTIC TREATMENT OF RESPIRATORY, CARDIAC AND OTHER PATHOLOGIES

(75) Inventors: Harry Fein, Nokomis, FL (US); Xueji Zhang, Sarasota, FL (US)

(73) Assignee: World Precision Instruments, Inc., Sarasota, FL (US)

( * ) Notice: Subject to any disclaimer, the term of this patent is extended or adjusted under 35 U.S.C. 154(b) by 0 days.

(21) Appl. No.: 09/884,786

(22) Filed: Jun. 19, 2001

(65) Prior Publication Data

US 2002/0192163 A1 Dec. 19, 2002

(51) Int. Cl.[7] .................................................. A61L 9/04
(52) U.S. Cl. ........................ 424/45; 424/43; 424/600; 424/718; 128/200.11; 128/200.12; 128/200.24; 514/958

(58) Field of Search .................... 128/200.24, 203.11, 128/203.12; 424/400, 43, 45, 600, 718; 514/958

(56) References Cited

U.S. PATENT DOCUMENTS 6,125,844 A * 10/2000 Samiotes ............... 128/200.12

* cited by examiner

Primary Examiner—Thurman K. Page
Assistant Examiner—Konata M. George
(74) Attorney, Agent, or Firm—Alix, Yale & Ristas, LLP

(57) ABSTRACT

A storage and delivery system for directly applying nitric oxide to a user includes a portable and disposable capsule and a source of nitric oxide gas disposed within the cavity. Gas flow control apparatus controls the flow of nitric oxide gas from the cavity. Gas flow initiation apparatus allows the user to initiate the flow of nitric oxide gas. The encapsulated nitric oxide gas is applied by positioning the capsule proximate to the objective site of the user and initiating flow of the nitric oxide gas.

36 Claims, 4 Drawing Sheets

METHODS AND APPARATUS FOR THERAPEUTIC TREATMENT OF RESPIRATORY, CARDIAC AND OTHER PATHOLOGIES

BACKGROUND OF THE INVENTION

The perception that nitric oxide (NO), a chemically active gas, plays an essential role in human and animal physiology was first demonstrated in 1987 with the publication of *Nitric Oxide Accounts for the Biological Activity of Endothelium Derived Relaxing Factor*; Palmer, R. M., Ferridge, A. G., Moncada, S; Nature 1987; 327:524–526. The authors demonstrated that the endothelial-derived relaxation factor (EDRF) was indeed nitric oxide. Many research publications have since defined more clearly the multiple and complex roles of NO in human, animal and plant physiology. Synthesized endogenously in humans, animals and plants, NO plays many very important physiological roles. For example, research reports have shown that NO may be effective in the treatment of sickle cell anemia.

Nitric oxide, in conjunction with ventilatory support and other appropriate agents, is used for the treatment of term and near-term (greater than 34 weeks) neonates with hypoxic respiratory failure associated with clinical or echocardiographic evidence of pulmonary hypertension, where it improves oxygenation and reduces the need for extracorporeal membrane oxygenation. It has also been reported to be useful as a selective pulmonary vasodilator in patients with adult respiratory distress syndrome. Lack of systemic vasodilatory effects with nitric oxide is an advantage over other vasodilators (e.g., epoprostenol (prostacyclin), nitroprusside).

Among the increasing range of pathologies which can be successfully treated with gaseous NO is anal disease. Anal fissure (or fissure-in-ano), anal ulcer, acute hemorrhoidal disease, and levator spasm (proctalgia fugax) are common, benign conditions of the anal canal which affect men and women. An anal fissure or ulcer is a tear or ulcer of the mucosa or lining tissue of the distal anal canal. An anal fissure/ulcer can be associated with other systemic or local diseases, but it is more frequently present as an isolated finding. The typical, idiopathic fissure or ulcer is confined to the anal mucosa, and usually lies in the posterior midline, distal to the dentate line. The person with an anal fissure or ulcer suffers from anal pain and bleeding, more pronounced during and after bowel movements.

Hemorrhoids are specialized vascular areas lying subjacent to the anal mucosa. Symptomatic hemorrhoidal disease is manifest by bleeding, thrombosis or prolapse of the hemorrhoidal tissues. Men and women are affected. Most commonly, internal hemorrhoidal tissue bulges into the anal canal during defecation causing bleeding. As the tissue enlarges, prolapse pain, thrombosis, and bleeding can ensue. Thrombosis of internal or external hemorrhoids is another cause of pain and bleeding.

Levator spasm (or proctalgia fugax) is a condition of unknown etiology affecting women more frequently than men. This syndrome is characterized by spasticity of the levator ani muscle, a portion of the anal sphincter complex. The patient suffering from levator spasm complains of severe, episodic rectal pain. Physical exam may reveal spasm of the puborectalis muscle. Pain may be reproduced by direct pressure on this muscle. Bleeding is not associated with this condition.

The underlying causes of these problems are poorly understood. However, all of these disorders are associated with a relative or absolute degree of anal sphincter hypertonicity. In the case of anal fissure/ulcer the abnormality appears to be an as yet unidentified problem of the internal and sphincter muscle. The internal sphincter is a specialized, involuntary muscle arising from the inner circular muscular layer of the rectum. Intra-anal pressure measurements obtained from people suffering from typical anal fissure/ulcer disease show an exaggerated pressure response to a variety of stimuli. The abnormally high intra-anal pressure is generated by the internal sphincter muscle. The abnormally elevated intra-anal pressure is responsible for non-healing of the fissure/ulcer and the associated pain. U.S. Pat. No. 5,504,117 teaches methods to treat anal pathologies by the topical application of preparations that stimulate the production of endogenous nitric oxide synthase (NOS) which, in turn, causes NO to be generated in endothelial tissue and in the nervous system, by the catalytic action of NOS upon L-Argenine.

Although safe NO dosage values are at present still evolving, the Occupational Safety and Health Administration (OSHA) has set the time-weighted average inhalation limit for NO at 25 ppm for 10 hours and $NO_2$ not to exceed 5 ppm. NIOSH Recommendations for Occupational Safety and Health Standards: Morbidity and Mortality Weekly Report, Vol. 37, No. S-7, p. 21(1988). The Environmental Protection Agency (EPA) has stated that a health-based national (maximum ambient) air quality standard for $NO_2$ is 0.053 ppm (measured as an annual average).

When exposed to oxygen, NO gas will, depending on environmental conditions, undergo oxidation to $NO_2$, also to higher oxides of nitrogen. Gaseous nitrogen dioxide, if inhaled in sufficient concentration (for example, as little as 10 ppm for ten minutes), is toxic to lung tissue and can produce pulmonary edema and this concentration and exposure time, or more, could result in death. Standards with regard to nitrogen dioxide toxicity have not been firmly established. Nitrogen dioxide is a deep lung irritant that can produce pulmonary edema and death if inhaled at high concentrations. The effects of $NO_2$ depend on the level and duration of exposure. Exposure to moderate $NO_2$ levels, 50 ppm for example, may produce cough, hemoptysis, dyspnea, and chest pain. Exposure to higher concentrations of $NO_2$ (greater than 100 ppm) can produce pulmonary edema, that may be fatal or may lead to bronchiolitis obliterans. Some studies suggest that chronic exposure to nitrogen dioxide may predispose to the development of chronic lung diseases, including infection and chronic obstructive pulmonary diseases.

It is common practice in therapeutic NO inhalation procedures both to monitor and also to remove $NO_2$ before it can be inhaled by a subject to whom NO is being applied. For example, the NO respiratory gas mixture may be transported through a soda lime mixture to scavenge nitrogen dioxide. However, NO gas in the therapeutic concentration range (i.e. 1 ppm to as much as 100 ppm) can be administered safely, for short time periods, in dry normal air (21% oxygen) without the formation of toxic concentrations of $NO_2$. Moreover, the present invention may include intracapsular means to adsorb $NO_2$.

Historically, NO gas is commercially manufactured using the Ostwald process (U.S. Pat. Nos. 4,774,069, 5,478,549) in which ammonia is catalytically converted to NO and Nitrous Oxide at a temperature above 800 degrees centigrade. This process thus involves the mass production of NO at high temperatures in an industrial setting. The therapeutic advantages of NO over other pulmonary and cardiovascular drugs have led researchers to attempt the design of an instrument that can deliver variable concentrations of NO accurately. For example, U.S. Pat. No. 5,396,882 describes a process for generating NO in an electric arc discharge in air where the electrodes are separated by an air gap in an arc chamber. The application of a high voltage across the air gap produces a localized plasma that breaks down oxygen and nitrogen molecules and generates a mixture of NO, ozone, and other NOx species. The concentration of NO in this system can be varied by adjusting the operating current. The gas mixture is then purified and mixed with air in order to obtain therapeutically significant concentrations of NO prior to administration to a patient. However, the quantification of generated NO by this system is purely empirical making the instrument extremely susceptible to the slightest fluctuations in the internal and external parameters such as ambient humidity and the surface area of the electrodes in the arc chamber.

Although inhalation of nitric oxide gas has been shown to be effective for treatment of pulmonary hypertension, there are several drawbacks and limitations of this particular mode of therapy. For example, current art therapy requires large and heavy gas tanks, expensive monitoring equipment, and a trained anesthesiologist to operate the tanks and equipment so as to deliver NO gas to a patient with safety. Therefore, NO inhalation therapy is at present limited to hospitals or similar clinical facilities. Thus there is a great needed for a more flexible, portable and less expensive means with which NO may be delivered safely in an organ specific manner without causing systemic vasodilation.

For over a century, nitroglycerin has been used as a vasodilating agent in the treatment of cardiovascular disease. Nitroglycerin, or glyceryl trinitrate, is an organic nitrate ester which when administered to a subject is converted biologically to nitric oxide by stimulating an enzyme, nitric oxide synthase (NOS), which in turn, catalyzes the production of endogenous NO from L-argenine. However, the effectiveness of nitroglycerin is greatly diminished because the recipient of therapeutic administration of nitroglycerin rapidly develops a tolerance to the beneficial effects of nitroglycerin. Therefore, onset of nitroglycerin tolerance significantly limits the therapeutic value of nitroglycerin because increased nitroglycerin dosages have little or no effect on vasorelaxation or vasodilatation. A further limitation may result from the fact that nitroglycerin is physiologically non specific. That is, vascular response to the drug will be generally distributed over the entire circulatory system.

SUMMARY OF THE INVENTION

The present invention teaches new and novel methods and means with which NO can be rapidly delivered to alveolar vascular tissue so as to bring about a rapid increase in the concentration of NO in lung and heart vascular epithelia. The effect is to cause rapid dilation of blood vessels in the lung and heart and to a considerably lesser degree, in more distal blood vessels through which blood circulates owing to the rapid absorption of NO by red blood cells.

The present invention features methods for prevention and treatment of asthma attacks and other forms of bronchial constriction, acute respiratory failure, or reversible pulmonary vasoconstriction (i.e., acute or chronic pulmonary vasoconstriction which has a reversible component). An affected subject may be identified, for example, by acute physical distress symptoms or by traditional diagnostic procedures. The subject will then inhale a therapeutically-effective concentration of gaseous nitric oxide so as to achieve therapeutic relief.

The present invention teaches methods and devices that produce NO from the inside of portable and disposable capsules containing NO under pressure and from chemical reagents which, when appropriately combined or activated, generate a controlled outflow of pure NO gas to the capsule exterior in free air. It is essential that the concentration of gas inhaled from the above mentioned capsular NO source be large enough to effect therapeutically beneficial results and at the same time not exceed a safe NO concentration maximum for gas inhalation. Both exposure time and gas concentration values together dictate what safe dosage may be.

The present invention teaches the principles of new devices and new procedures that will provide effective therapeutic application of inhaled NO during coronary and respiratory emergencies such as angina, thrombosis in heart and lung blood vessels; also hypertension in lung vasculature, as well as reversible asthma attacks.

BRIEF DESCRIPTION OF THE DRAWINGS

The present invention may be better understood and its numerous objects and advantages will become apparent to those skilled in the art by reference to the accompanying drawings in which.

DETAILED DESCRIPTION OF THE PREFERRED EMBODIMENTS

A number of compounds have been developed that are capable of delivering nitric oxide in a pharmacologically useful way. Such compounds include compounds that release nitric oxide after being metabolized and compounds that release nitric oxide spontaneously in aqueous solutions. Compounds capable of releasing NO upon being metabolized include the widely used nitrovasodilators glyceryl trinitrate (nitroglycerin) and sodium nitroprusside (SNP). These compounds are relatively stable but they release or cause the release of NO upon activation.

Many nitric oxide-nucleophile complexes also have been described. Some of these compounds, known as NONOates, evolve nitric oxide upon heating or hydrolysis. These compounds, unlike nitroglycerin or SNP, release NO without requiring activation. NONOates have reproducible half-lives ranging from 2 seconds to 20 hours. Nitricoxide/nucleophile complexes (NONOates) that release nitric oxide in aqueous solution are disclosed in U.S. Pat. Nos. 5,389, 675, 5,366, 977, and 5,250, 550. The nitric oxide-releasing functional group is R-[NONO], where R is an organic or inorganic moiety bonded to the [NONO].

NO may be generated from S-nitrosothiols (RSNO) in presence of catalyst Cu(1), as outlined in the reaction below:

$$2RSNO \rightarrow 2NO + RS-SR \qquad (1)$$

The concentration of generated NO is equal to the original RSNO concentration after the addition of the catalyst Cu(I).

NO may be generated chemically. In a first example, based on the reaction of nitrite with iodide in an acidic medium as in the reaction:

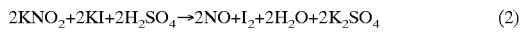

$$2KNO_2 + 2KI + 2H_2SO_4 \rightarrow 2NO + I_2 + 2H_2O + 2K_2SO_4 \qquad (2)$$

The concentration of NO is determined by the nitrite and iodide concentrations. Ascorbic acid may be used above to replace KI as a reductant.

In a second example, at room temperature, vanadium (III) rapidly reduces nitrite to nitric oxide in an acidic solution. Vanadium (III), as a reductant is oxidized to vanadium (IV):

$$NO_2^- + 2H^+ + e \rightarrow NO + H_2O \qquad (3)$$

Figure 1:
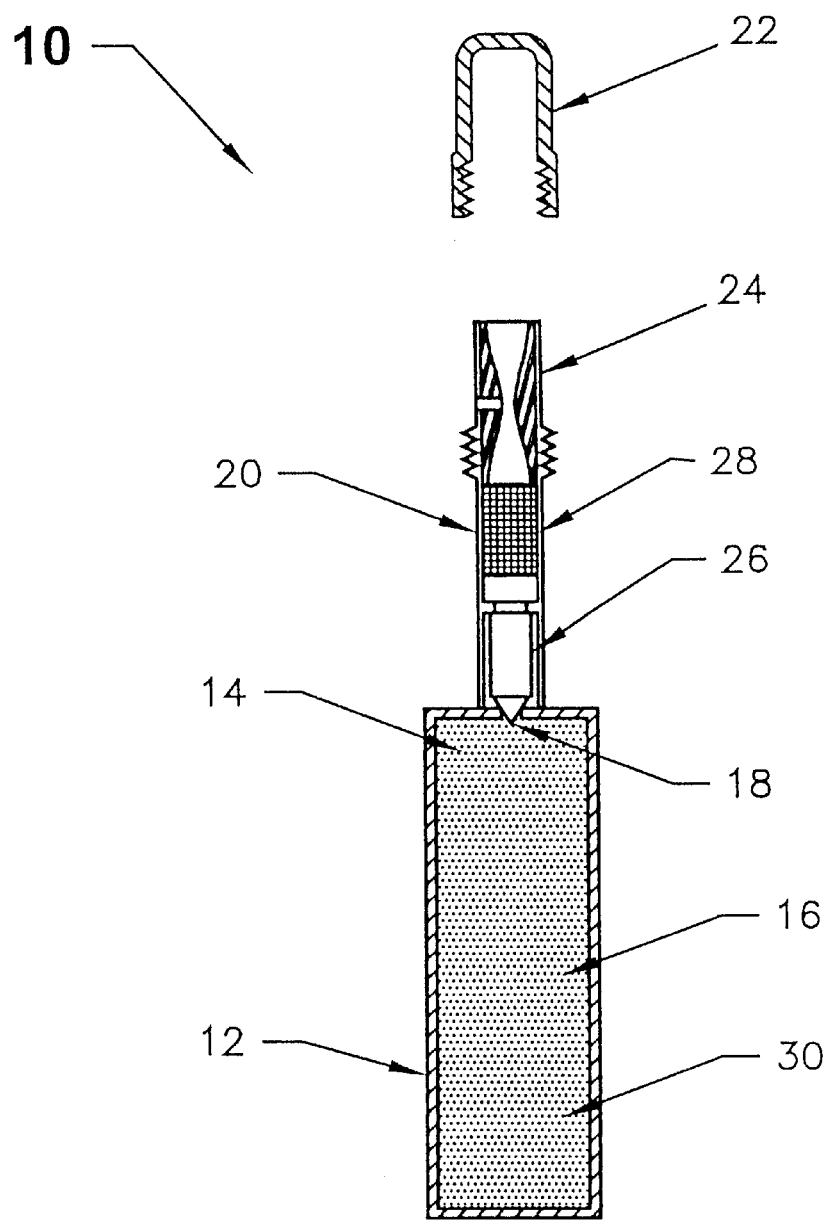
FIG. 1 is a schematic, cross-sectional view of a first embodiment of a NO storage and delivery system in accordance with the invention.

The NO storage and delivery system 10 shown in FIG. 1 employs a gas impermeable capsule 12 as the storage vessel for a gas source 14 composed of compressed NO gas. NO gas is injected into the capsule 12 under pressure in an anaerobic environment. The internal gas-filled cavity 16 has preferably a 1 to 5 ml inner volume. Internal NO gas pressure is typically 15 to 30 psi. The capsule casing is impermeable to gas leakage.

Gas is released from the capsule 12 via an opening 18 extending through the capsule wall and an applicator sleeve 20 enclosing the opening 18 and extending outwardly from the capsule 12. Gas release can be effected, for example, by removal of a gas-tight cap 22 from the neck 24 of the applicator sleeve 20. Alternative capsule sealing methods can be easily implemented by conventional art means.

A miniature pressure controller 26 within the sleeve 20 limits the exit pressure of the stored gas so as to release NO gas at a constant pressure which is less than that of the initial internal capsule gas pressure. An outlet filter 28 downstream of the pressure controller 26 restricts the rate of gas outflow. For example, gas release pressure regulated at 5 psi would be adequate to assure constant gas outflow for periods of time which can be made to range from a few seconds to hours. The flow rate of exiting gas can be limited to a few micro liters per minute. Prior to use, the capsule 12 is stored in a sterile bag that is gas and moisture impermeable to prevent environmental and bacterial infiltration.

As an alternative to charging the capsule 12 from an external pressurized NO gas source, the NO gas source 14 can be a NO bearing polymer. The polymer material is sealed within the capsule cavity 16 and slowly decomposes to release the NO gas stored therein, and thus constitutes the intra capsular NO gas supply 14. The polymer material is initially loaded into the capsule 12 in an oxygen-free environment. If NONOate is to be the NO source 14, de-aerated water must be applied to initiate NO release.

Figure 2:
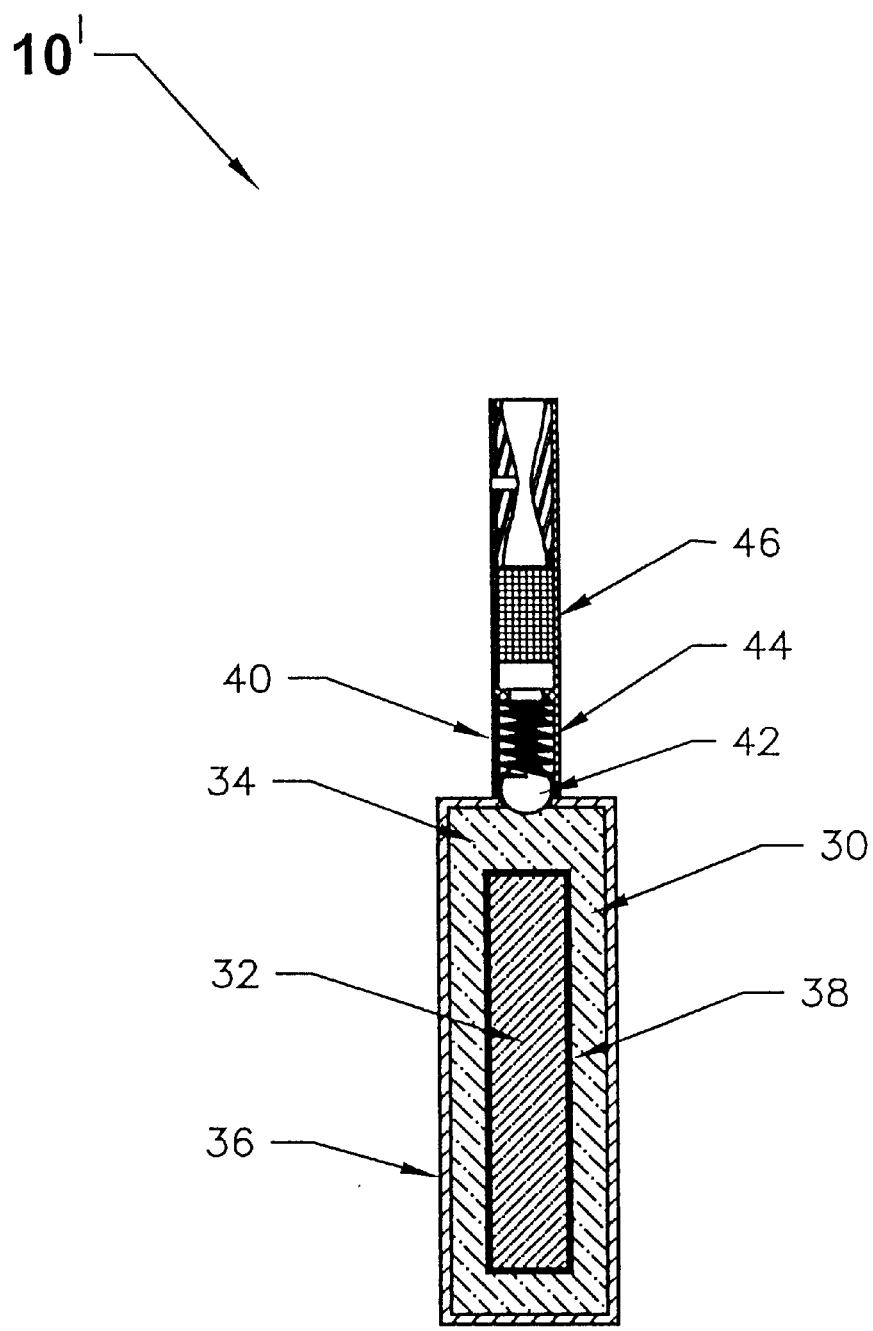
FIG. 2 is a schematic, cross-sectional view of a second embodiment of a NO storage and delivery system in accordance with the invention.

FIG. 2 illustrates a second embodiment of the system 10' having a NO gas source 30 in which NO gas is created by activation of stored chemical reagents 32, 34. Capsule 36 is flexible and gas impermeable. The gas source 30 comprises stored reagents 32 and 34, which are physically isolated by a breakable divider 38, for example a glass tube, containing reagent 32. Bending capsule 38 breaks reagent vessel 38 causing chemical reagents 32 and 34 to mix, resulting in the rapid formation of NO gas within the capsule 36. The known stoichiometry of the chemical reaction and the volume of the capsule interior allows accurate prediction of the resulting intra capsular NO gas pressure. A single example of several feasible chemical reactions is illustrated in equation (1) above. In this example, reagent 32 is a solution of potassium nitrite and reagent 34 is a mixture of potassium iodide and sufric acid.

Compressed NO gas flows out of the capsule 36 via a check valve 40 comprised, for example, by a ball 42 and spring 44. The outflow filter 46 controls the gas outflow rate and also filters water vapor from the fluid reagents in the capsule 36. The filter 46 may be treated with a nitrogen dioxide adsorbent so as to insure that, if present, virtually no nitrogen dioxide will be present in the generated gas. Prior to use, the capsule 36 is stored in a sterile bag that is gas and moisture impermeable to prevent environmental and bacterial infiltration.

Figure 3:
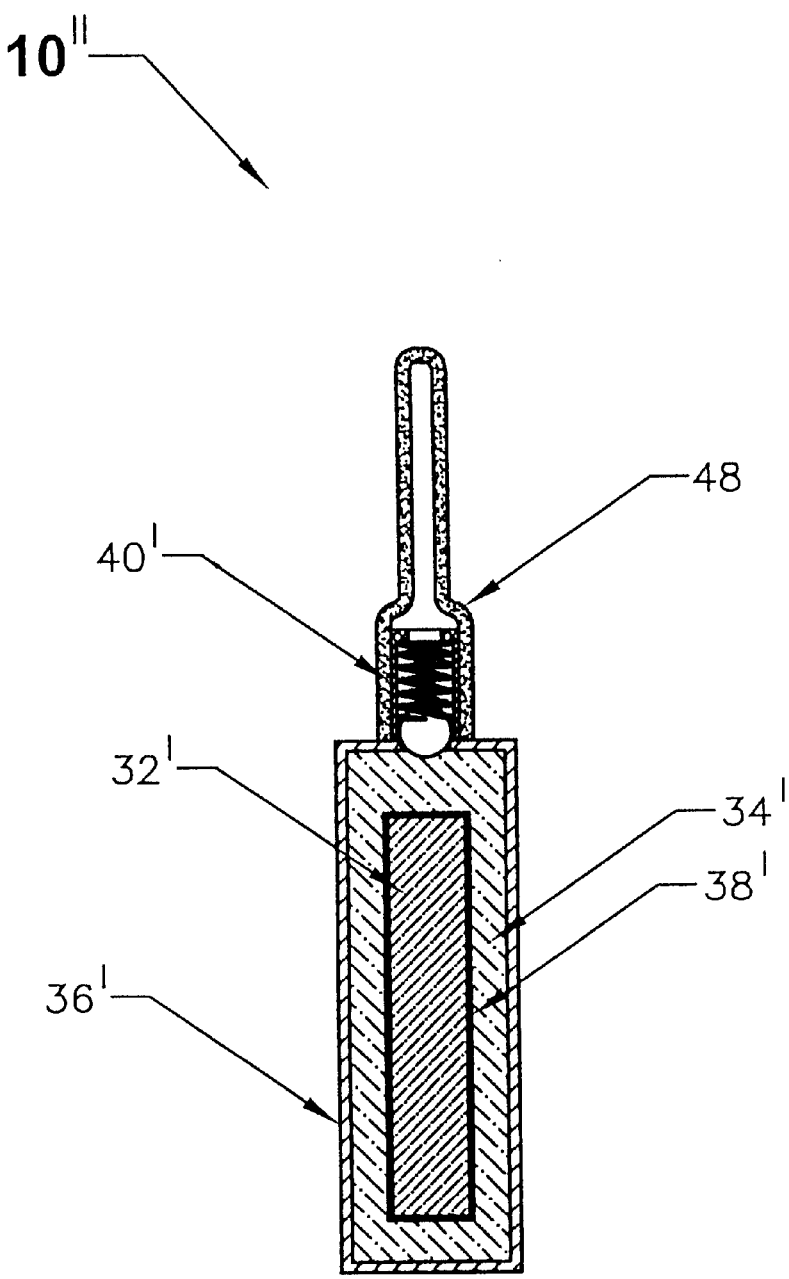
FIG. 3 is a schematic, cross-sectional view of a third embodiment of a NO storage and delivery system in accordance with the invention.

The embodiment 10" shown is FIG. 3 is similar in form and function to the embodiment 10' of FIG. 2 except that outlet filter 46 of FIG. 2 is replaced by a NO gas permeable capped tube 48 which delivers a diffuse gentle flow of NO into the nostrils or, alternatively, other body cavities of subject humans or animals for therapeutic effect. Internal tubular gas pressure and the gas permeability of the capped tube 48 both determine the rate of the resulting NO gas outflow. Prior to use, the capsule 36 is stored in a sterile bag that is gas and moisture impermeable to prevent environmental and bacterial infiltration.

Figure 4:
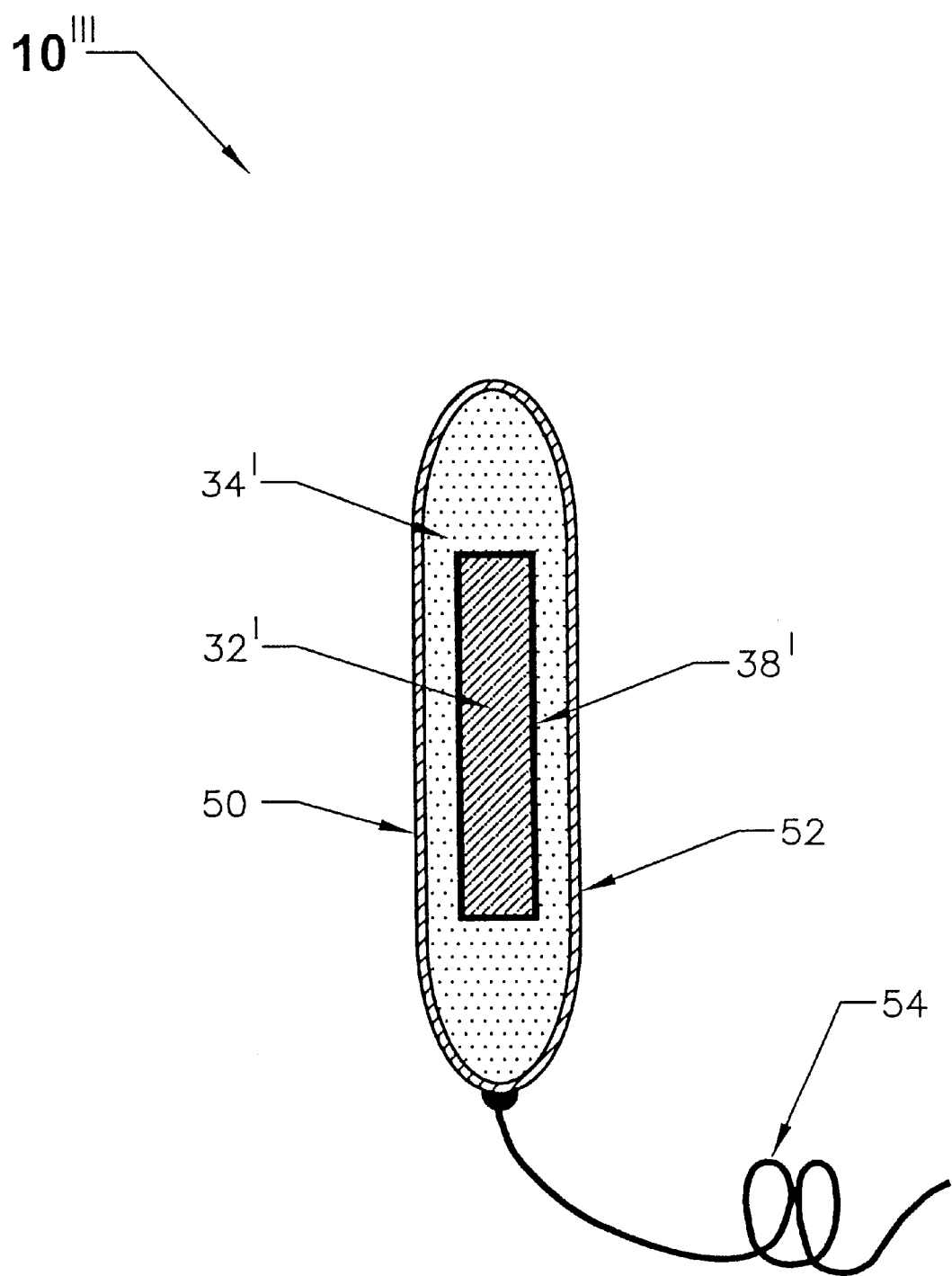
FIG. 4 is a schematic, cross-sectional view of a fourth embodiment of a NO storage and delivery system in accordance with the invention.

The embodiment 10''' illustrated in FIG. 4 has an ovoid or lozenge shaped capsule 50. The capsule 50 is impermeable to acid or water or other interior reagents 32, 34 employed therein. The capsule 50 is also NO gas permeable and flexible. Active chemical reagents 32' and 34' are similar in function to reagents 32 and 34 of FIG. 2. Reagent 32' is contained in a breakable compartment 38' or tube as in FIG. 2. In use, the capsule 50 is activated by applying sufficient force to break the reagents tube 38' which initiates a NO gas producing reaction as discussed above. After activation, the capsule 50 may be lubricated with a gas permeable fluid 52 such as silicone and gently inserted into the appropriate body cavity of a subject requiring NO gas therapy as discussed above. Upon completion of the NO treatment, the capsule 50 may be withdrawn by using the attached cord 54. For respiratory therapy, the capsule 50 may be held under the nostrils for the duration of the treatment. Prior to use, the capsule 50 is stored in sterile bags that are gas and moisture impermeable to prevent environmental or bacterial infiltration and possible contamination.

It should be appreciated that by using a system 10, 10', 10", 10"Δ in accordance with the invention, pure NO gas is generated for inhalation proximal to or within the nostrils of the subject and transported to the lungs by the tidal action of the subject's respiration. The concentration of nitric oxide gas is diluted by the respiratory tidal volume of the user. Consequently, the user's own respiration performs the dual function of transporting and diluting the NO gas. Moreover, negligible nitrogen dioxide formation occurs within the time interval in which NO gas is transported by the respiratory tidal volume to the lung alveoli. Theoretical analysis and experimental results indicate the $NO_2$ concentration is much less than 1 ppm for the time periods used by the inventive methods of the present invention. It should also be appreciated that the subject system 10, 10', 10", 10''' does not require an expensive and complex gas mixing and delivery system because the subject's own respiration safely delivers NO gas at low ppm concentration levels to the subject's lungs. It should further be appreciated that the subject system 10, 10', 10", 10''' does not utilize industrial NO gas tanks, which are expensive, heavy and potentially dangerous.

The above disclosed embodiments are generally single use systems with the amount of pressurized NO gas or reagents sized accordingly. It should be appreciated that once the reagents of embodiments 10', 10", and 10''' are mixed together, the resulting reaction will continue to completion. Further, the absence of a gas-tight cap 22 on the applicator sleeve of the second embodiment 10' and the permeable nature of the capped tube 48 of the third embodiment 10", and the capsule 50 of the fourth embodiment 10'" preclude retention of the NO gas within the capsule 36, 36', 50 after the reagents 32, 32', 34, 34' have been mixed. While it is possible that the gas-tight cap 22 of the first embodiment 10 may be replaced before all of the pressurized NO gas is dispensed through the applicator sleeve 20, the escaping NO gas will interfere with such replacement and there is no way of assuring that the remaining amount of NO gas will be therapeutically useful.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A nitric oxide storage and delivery system for directly applying the nitric oxide to a user, the system comprising:
   a portable and disposable capsule defining a cavity;
   a tube having a passageway communicable with said cavity and defining an outlet;
   a source of nitric oxide gas disposed within the cavity;
   gas flow control apparatus adapted for controlling a flow of nitric oxide gas from the cavity; and
   gas flow initiation means for user initiation of the flow of nitric oxide gas,
   wherein substantially pure nitric oxide gas is selectively supplied to the outlet.

2. The system of claim 1, wherein the capsule is composed of a gas impermeable material, and the source of nitric oxide gas is a volume of pressurized nitric oxide gas filling the cavity.

3. The system of claim 2, further comprising an applicator sleeve defining a bore, wherein the capsule defines an opening, the applicator sleeve extends from a proximal end enclosing the opening of the capsule to a distal end and the gas flow initiation means comprises a gas-tight cap removably mounted to the distal end of the applicator sleeve.

4. The system of claim 3, wherein the gas flow control apparatus comprises a pressure controller disposed within the bore of the applicator sleeve.

5. The system of claim 4, wherein the gas flow control apparatus further comprises an outlet filter disposed within the bore of the applicator sleeve intermediate the pressure controller and the distal end.

6. The system of claim 1, wherein the capsule is composed of a gas impermeable material, and the source of nitric oxide gas is a nitric oxide bearing polymer which decomposes to release the nitric oxide gas stored therein.

7. A nitric oxide storage and delivery system for directly applying the nitric oxide to a user, the system comprising:
   a portable and disposable capsule defining a cavity;
   a source of nitric oxide gas disposed within the cavity, said source of nitric oxide gas comprising first and second reagents and a separator selectively separating the first reagent from the second reagent, the first and second reagents forming nitric oxide gas when mixed;
   gas flow apparatus adapted for controlling the flow of nitric oxide gas from the cavity; and
   gas flow initiation means for user initiation of the flow of nitric oxide gas.

8. The system of claim 7 wherein the separator comprises a breakable container disposed within the cavity of the capsule, the first reagent being stored in the cavity of the capsule and the second reagent being stored within the container.

9. The system of claim 7 wherein the first reagent is a solution of potassium nitrite and the second reagent is a mixture of potassium iodide and sufric acid.

10. The system of claim 7, further comprising an applicator sleeve defining a bore, wherein the capsule is composed of a gas impermeable material and defines an opening, the applicator sleeve extends from a proximal end enclosing the opening of the capsule to a distal end and the gas flow initiation means comprises a check valve disposed within the bore of the applicator sleeve proximate to the opening of the capsule.

11. The system of claim 10, wherein the gas flow control apparatus comprises an outflow filter disposed within the bore of the applicator intermediate the check valve and the distal end.

12. The system of claim 11, wherein the outflow filter includes a nitrogen dioxide adsorbent.

13. The system of claim 7, further comprising a nitric oxide gas permeable capped tube, wherein the capsule is composed of a gas impermeable material and defines an opening, the capped tube extending from a proximal end enclosing the opening of the capsule to a capped end, and the gas flow initiation means comprises a check valve disposed within the capped tube proximate to the opening of the capsule.

14. The system of claim 13, wherein the amounts of the first and second reagents and the permeability of the capped tube are selected to provide a predetermined nitric oxide gas flow rate.

15. The system of claim 7, wherein the capsule has an ovoid shape and is composed of a material which is impermeable to acid, water, and the first and second reagents but which is nitric oxide gas permeable.

16. The system of claim 15, wherein the capsule is flexible.

17. The system of claim 15, further comprising a cord having oppositely disposed first and second ends, the first end of the cord being mounted to the capsule.

18. The system of claim 1, wherein the system is a single use system.

19. A single use nitric oxide storage and delivery system for directly applying the nitric oxide to a user, the system comprising:
   a portable and disposable capsule composed of a gas impermeable material and defining a cavity and an opening extending from the cavity;
   an applicator sleeve defining a bore and extending from a proximal end enclosing the opening of the capsule to a distal end;
   a source of nitric oxide gas disposed within the cavity;
   a gas-tight cap removably mounted to the distal end of the applicator sleeve; and
   gas flow control apparatus disposed in the bore of the applicator sleeve.

20. The system of claim 19, wherein the source of nitric oxide gas is a volume of pressurized nitric oxide gas filling the cavity.

21. The system of claim 19, wherein the gas flow control apparatus comprises a pressure controller disposed within the bore of the applicator sleeve and an outlet filter disposed within the bore of the applicator sleeve intermediate the pressure controller and the distal end.

22. The system of claim 19, wherein the source of nitric oxide gas is a nitric oxide bearing polymer which decomposes to release the nitric oxide gas stored therein.

23. A single use nitric oxide storage and delivery system for directly applying the nitric oxide to a user, the system comprising:

a portable and disposable capsule defining a cavity;

a breakable container disposed within the cavity of the capsule;

first and second reagents, the first reagent being stored in the cavity of the capsule and the second reagent being stored within the container; and gas flow control apparatus adapted for controlling a flow of nitric oxide gas from the cavity;

wherein the first and second reagents form nitric oxide gas when the container is broken to mix the reagents.

24. The system of claim 23, wherein the capsule defines an opening and the gas flow control apparatus comprises an outflow filter disposed proximate to the opening of the capsule.

25. The system of claim 23, wherein the capsule defines an opening and the gas flow control apparatus comprises a nitric oxide gas permeable capped tube, the permeability of the capped tube being selected to provide a predetermined nitric oxide gas flow rate.

26. The system of claim 23, wherein the capsule is composed of a flexible material which is impermeable to acid, water, and the first and second reagents but which is nitric oxide gas permeable, the permeability of the capsule being selected to provide a predetermined nitric oxide gas flow rate.

27. A method of therapeutically applying nitric oxide gas comprising the steps of:

encapsulating a source of nitric oxide gas in a cavity of a portable, disposable capsule, the capsule having a tube defining a passageway having an output end and gas flow control apparatus adapted for controlling a flow of nitric oxide gas from the capsule through the output end and gas flow initiation means for user initiation of the flow of nitric oxide gas;

positioning the capsule proximate to an objective site of the user; and initiating flow of the nitric oxide gas comprising breaking the container so that substantially pure nitric oxide gas exits the output end.

28. The method of claim 27 wherein the step of encapsulating a source of nitric oxide gas includes injecting nitric oxide gas into the cavity of the capsule under pressure in an anaerobic environment.

29. The method of claim 27 wherein the step of encapsulating a source of nitric oxide gas includes inserting a nitric oxide bearing polymer into the cavity of the capsule in an anaerobic environment.

30. The method of claim 27 wherein the capsule also has a container disposed in the cavity and the source of nitric oxide gas comprises a first reagent stored in the cavity of the capsule and a second reagent stored within the container, the first and second reagents forming nitric oxide gas when mixed and wherein the step of initiating flow of the nitric oxide gas includes breaking the container.

31. The method of claim 27 wherein the step of positioning the capsule includes inserting the capsule into a passage of the user.

32. The method of claim 27 further comprising the step of regulating the flow of the nitric oxide gas.

33. The method of claim 27 further comprising the step of diluting the flow of nitric oxide gas with the respiratory tidal volume of the user.

34. A nitric oxide storage and delivery system for directly applying the nitric oxide to a user, the system comprising:

a portable and disposable capsule defining a cavity, the capsule being disposed of a gas impermeable material;

a source of nitric oxide gas disposed within the cavity, the source of nitric oxide gas being a nitric oxide bearing polymer which decomposes to release the nitric oxide gas stored therein;

gas flow control apparatus adapted for controlling a flow of nitric oxide gas from the cavity; and gas flow initiation means for user initiation of the flow of nitric oxide gas.

35. A method of therapeutically applying nitric oxide gas comprising the steps of:

encapsulating a source of nitric oxide gas in a cavity of a portable, disposable capsule, the capsule having gas flow control apparatus adapted for controlling a flow of nitric oxide gas from the capsule and gas flow initiation means for user initiation of the flow of nitric oxide gas, said encapsulating including injecting a nitric oxide bearing polymer into the cavity of the capsule in an anaerobic environment;

positioning the capsule proximate to an objective site of the user; and initiating flow of the nitric oxide gas.

36. A method of therapeutically applying nitric oxide gas comprising the steps of:

encapsulating a source of nitric oxide gas in a cavity of a portable, disposable capsule, the capsule having a tube defining a passageway having an output end and gas flow control apparatus adapted for controlling a flow of nitric oxide gas from the capsule and gas flow initiation means for user initiation of the flow of nitric oxide gas, a container being disposed in the cavity and the source of nitric oxide gas comprises a first reagent stored in the cavity of the capsule and a second reagent stored within the container, the first and second reagents forming nitric oxide gas when mixed;

positioning the capsule proximate to an objective site of the user; and initiating flow of the nitric oxide gas so that substantially pure nitric oxide gas exits the output end.

* * * * *

UNITED STATES PATENT AND TRADEMARK OFFICE
CERTIFICATE OF CORRECTION

PATENT NO.    : 6,749,834 B2
DATED         : June 15, 2004
INVENTOR(S)   : Fein et al.

It is certified that error appears in the above-identified patent and that said Letters Patent is hereby corrected as shown below:

Column 7,
Line 22, delete "tube" and insert -- applicator sleeve --.
Line 28, delete "gas flow initiation means" and insert -- gas-tight cap removably mounted --.
Line 31, delete "to" and insert -- through --.
Lines 39-40, delete "the gas flow initiation means comprises".
Line 40, after "cap" insert -- is --.

Signed and Sealed this

Twenty-fourth Day of January, 2006

JON W. DUDAS
*Director of the United States Patent and Trademark Office*